United States Patent [19]

Anderson

[11] 4,109,320
[45] Aug. 29, 1978

[54] ATTACHING ASSEMBLY

[75] Inventor: Marshall N. Anderson, Grayslake, Ill.

[73] Assignee: Sellstrom Manufacturing Company, Palatine, Ill.

[21] Appl. No.: 805,537

[22] Filed: Jun. 10, 1977

[51] Int. Cl.² .................................... A61F 9/06
[52] U.S. Cl. ............................ 2/10; 24/206 R; 403/94; 403/95
[58] Field of Search ............... 2/8, 5, 10, 424; 24/230 R, 3 R, 230 AK, 206 R; 403/384, 83-97

[56] References Cited

U.S. PATENT DOCUMENTS

| 3,021,527 | 2/1962 | Larsen | 2/10 X |
| 3,205,522 | 9/1965 | Then | 403/97 X |
| 3,332,086 | 7/1967 | Simpson et al. | 2/10 X |
| 3,375,529 | 4/1968 | Timm et al. | 2/8 |
| 3,946,466 | 3/1976 | Sakai | 2/10 X |

*Primary Examiner*—Werner H. Schroeder
*Assistant Examiner*—Moshe I. Cohen
*Attorney, Agent, or Firm*—Neuman, Williams, Anderson & Olson

[57] ABSTRACT

An assembly is provided which is adapted to be used in attaching a secondary unit, such as a face protective device, to a primary unit, such as a safety helmet. The helmet is of rigid material and has the lower peripheral edge thereof provided with a flange forming a gutter or trough. A gap is formed in the flange so as to enable the assembly to be slidably mounted on and removed from the primary unit flange. The assembly includes a bracket having a base portion adapted to be in slidable supporting engagement with a segment of the exterior wall surface of the primary unit. The bracket also includes a first extension extending laterally from the base portion and slidably positioned within the trough at a predetermined location, and a second extension offset from said first extension and disposed outside the trough and in sliding engagement with the flange. The extensions coact with one another to resiliently grip the flange therebetween and retain the bracket in the predetermined location. Coacting with the bracket base portion is a means for connecting thereto the secondary unit.

20 Claims, 19 Drawing Figures

U.S. Patent    Aug. 29, 1978    Sheet 1 of 3    4,109,320
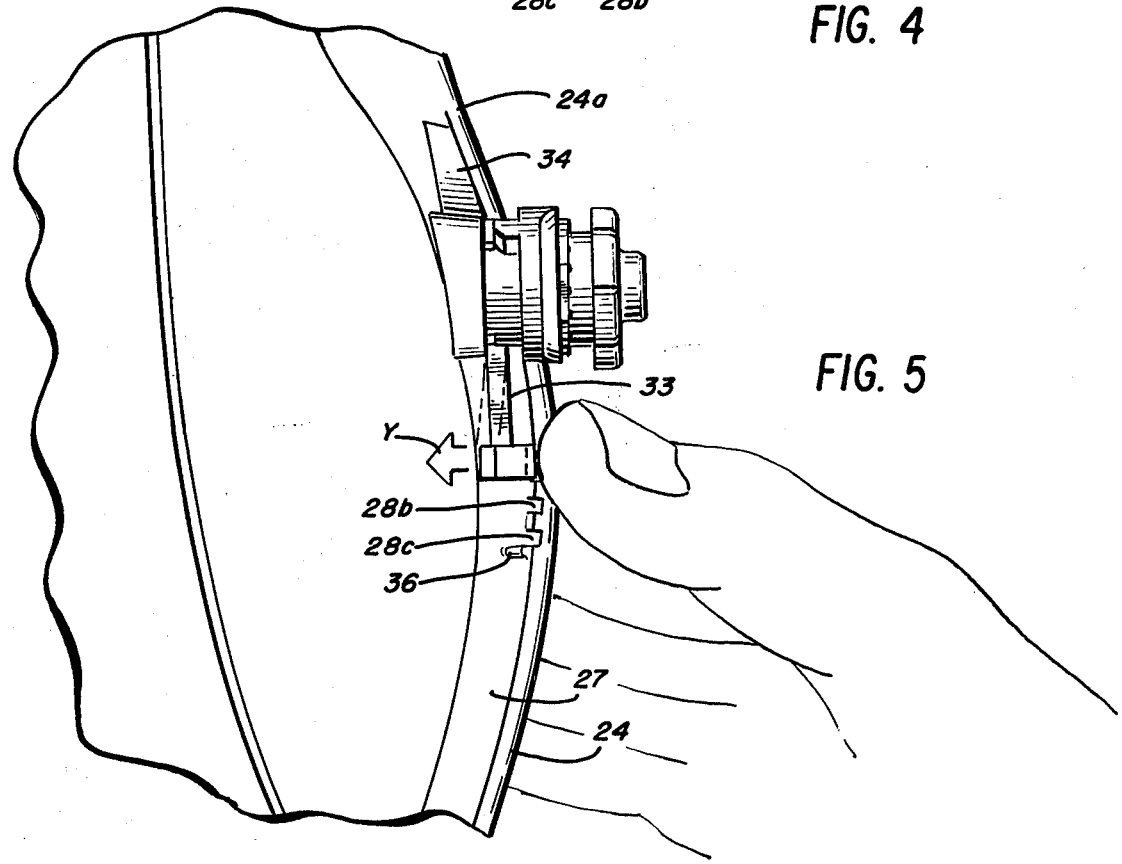

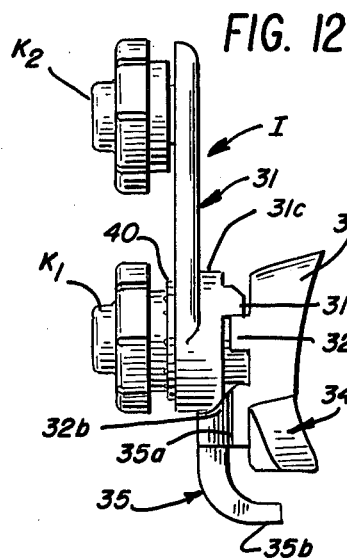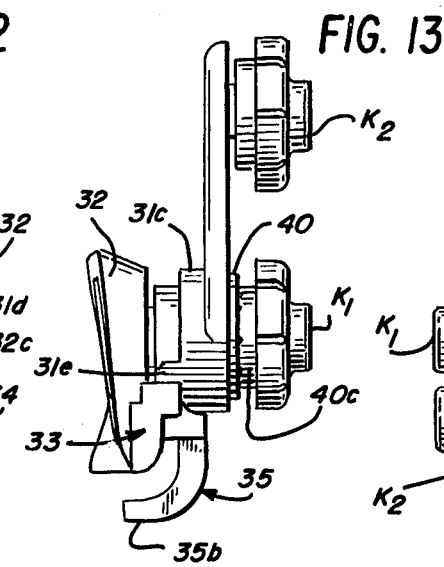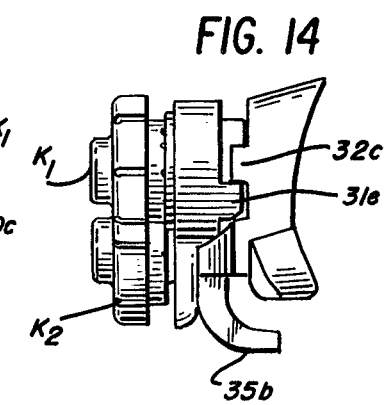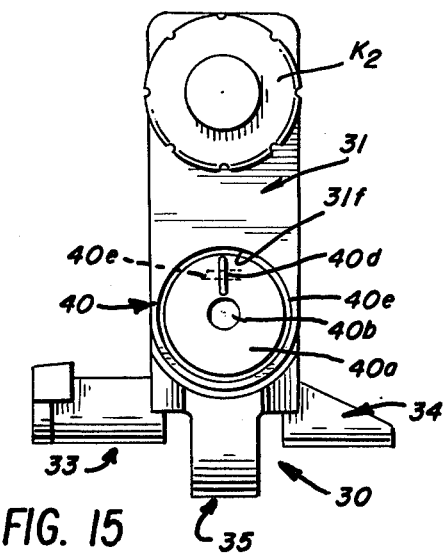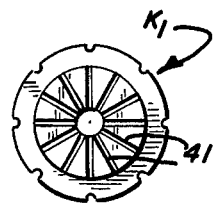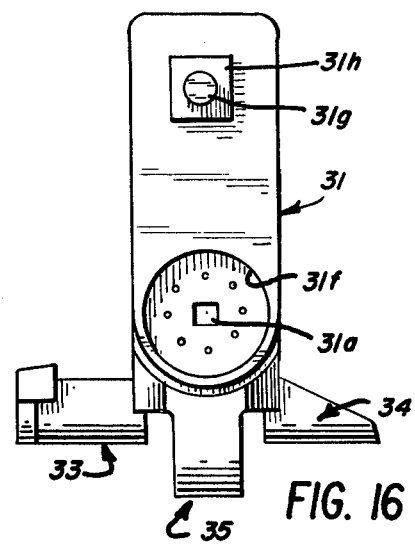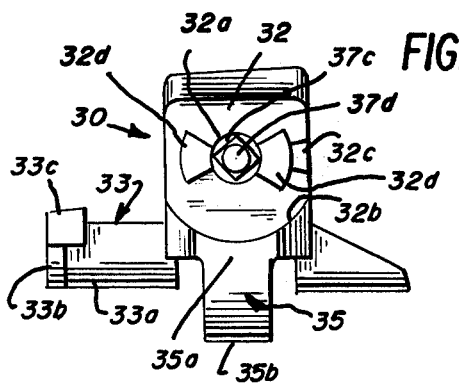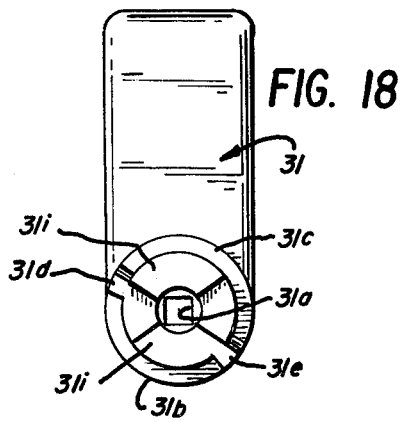

ATTACHING ASSEMBLY

BACKGROUND OF THE INVENTION

The utilization of safety helmets, sometimes referred to as hard hats, by persons engaged in certain types of activities or located in certain areas, has become a safety requirement which is normally strictly enforced by governmental, quasi-governmental and/or private agencies and companies. Oftentimes the wearer of such a helmet requires the use of an additional protective device (e.g., welder's mask, face shield, goggles, noise reducing earmuffs, etc.). The utilization of such protective devices has frequently in the past involved either removal of the safety helmet, thereby exposing the wearer to certain safety hazards, or required a special type of safety helmet with built-in means designed to accommodate only a particular type of protective device. In some instances the safety helmets were provided with protruding brackets mounted in fixed locations on the exterior of the helmet, thereby increasing the manufacturing cost of such helmet and requiring all of the protective devices to be mounted in precisely the same location relative to the helmet. Because of the fixed location of the protective device on the helmet, the effectiveness thereof in providing the necessary protection was impaired and/or the helmet with the protective device attached was uncomfortable and unstable when worn.

In other prior constructions it was difficult to maintain a secure connection between the helmet and protective device and thus required frequent manual adjustment by the user. Furthermore, the earlier constructions were of complex design, susceptible to malfunction, and to substitute or replace either the helmet or protective device was an awkward, time consuming operation.

SUMMARY OF THE INVENTION

Thus, it is an object of the invention to provide an attaching assembly which is of simple, lightweight construction; is capable of being used with a wide variety of primary and secondary units; and may be readily adjusted without requiring special tools or the like.

It is a further object of the invention to provide an attaching assembly which permits ready adjustment of one unit relative to the other so as to enhance the comfort and safety of the person utilizing the helmet and protective device.

It is a still further object of the invention to provide an attaching assembly which readily complies with existing safety regulations, is capable of withstanding abusive treatment, and is functional under severe climatic and/or environmental conditions.

It is a still further object of the invention to provide an attaching assembly which does not require modifications to be made to a helmet in order to accommodate the assembly, and which does not adversely affect the esthetic appeal and structural integrity of the helmet.

Further and additional objects will appear from the description, accompanying drawings, and appended claims.

In accordance with one embodiment of the invention, an assembly is provided for removably attaching a secondary unit to a primary unit. The primary unit is provided with an exterior wall surface and an exposed flange connected thereto and extending therefrom and disposed in spaced, substantially face-to-face relation with respect to the exterior wall surface. The assembly includes a bracket having a base portion which slidably engages the exterior wall surface. Extending laterally from the base portion is a first extension which is slidably disposed within the space formed between the flange and the exterior wall surface. A second extension is also provided which is offset from the first extension and extends from the bracket base portion over the flange and slidably engages the exterior surface of the flange. The first and second extensions coact with one another and resiliently grip the flange and retain the bracket in a predetermined position on the primary unit. The assembly also includes manually adjustable means which connect the secondary unit to the bracket base portion.

DESCRIPTION

For a more complete understanding of the invention, reference should be made to the drawings, wherein:

FIG. 1 is a perspective side view of one form of the attaching assembly in combination with a safety helmet and a welder's mask, the latter being shown in full lines in an inoperative position and in phantom lines in an operative position.

FIG. 2 is a side elevational view of FIG. 1 but with the welder's mask removed.

FIG. 3 is a fragmentary top view of FIG. 2.

FIG. 4 is an enlarged fragmentary view of the attaching assembly of FIG. 1 shown being mounted on the safety helmet.

FIG. 5 is an enlarged fragmentary view of the attaching assembly of FIG. 1 shown being manually disassembled from the safety helmet.

FIG. 12 is a right side elevational view of the attaching assembly of FIG. 7.

FIG. 13 is a left side elevational view of the attaching assembly of FIG. 7.

FIG. 14 is a right side elevational view of the attaching assembly of FIG. 8.

FIG. 15 is a front elevational view of the attaching assembly of FIG. 7 with the lower adjusting knob removed therefrom.

FIG. 15a is a rear elevational view of the knob removed in FIG. 15.

FIG. 16 is similar to FIG. 15 but with a friction means and an upper adjusting knob removed.

FIG. 17 is like FIG. 16 but with a link member removed and showing only the front side of the bracket to which the link member was connected.

FIG. 18 is a rear elevational view of the link member removed in FIG. 17.

Figure 6:
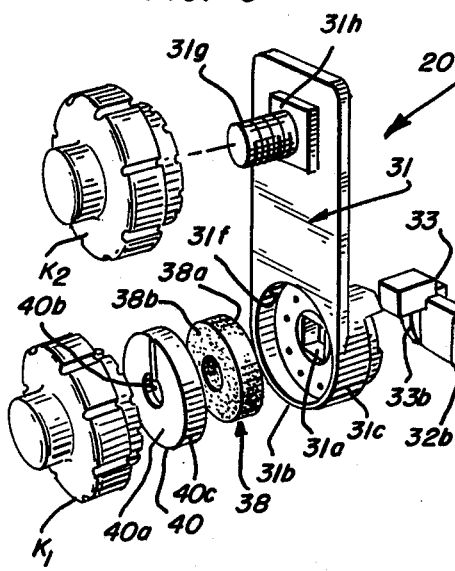
FIG. 6 is an exploded perspective view of the attaching assembly of FIG. 1.

Referring now to the drawings and more particularly to FIG. 1, one form of the improved attaching assembly 20 is shown mounted on a safety helmet 21 and connecting thereto a welder's mask 22. While the assembly 20 is shown in combination with the helmet and welder's mask, its use and function are not limited thereto. The application of the assembly 20 for use in connecting various types of secondary units to various types of primary units will become apparent from the discussion to follow.

The use of safety helmets 21 in construction work, mining, and in numerous other diverse vocational and avocational activities wherein bodily injury to the head of the participant is likely to occur, has become mandatory or recommended by either governmental, quasi-governmental, and/or private rules or regulations so as to enhance personal safety. The helmet is normally molded of a strong, hard, lightweight plastic (e.g., nylon) and includes a crown portion 23, a flange 24 connected to and substantially encompassing the lower periphery of the crown portion, and a visor 25 which interrupts the flange 24 and extends forwardly from the front side of the helmet. Disposed within the interior of the crown portion 23 is a slinglike headpiece 26 having the headband 26a thereof adjustable to comfortably accommodate the head of the wearer, see FIG. 2. The interior surface of the helmet crown portion 23 is provided with a plurality of slotted brackets, not shown, which are adapted to removably accommodate lugs carried by the headpiece 26. The lugs may be readily assembled on or disassembled from the slotted brackets when the helmet is to be worn with the visor 25 thereof extending rearwardly from the head of the wearer. Such an arrangement is quite common, when a welder's mask 22 is attached to the helmet, see FIG. 1, because it enables the mask to be positioned closer to the face of the wearer. Where other protective (secondary) devices, such as face masks, goggles, noise reducing earmuffs, etc., are attached to the helmet by the assembly 20, the helmet is normally worn with the visor 25 facing forwardly.

It will be noted in FIGS. 1–5 that the ends 24a of flange 24 taper into the visor 25 at opposite sides thereof. This configuration of the flange ends 24a is of importance in facilitating mounting and removing of the assembly 20 with respect to the helmet flange 24. The flange 24 is disposed in a spaced substantially face-to-face relation with the exterior surface of the crown portion 23, and the lower edges of the flange and crown portion periphery are interconnected by an imperforate web 27. The flange 24, the web 27, and the exterior surface of the crown portion 23 cooperate to form a gutter or trough T which not only catches water or other liquid striking the crown portion, but also serves to reinforce the lower portion of the helmet.

It will be noted in FIGS. 4 and 5 that the surface of flange 24, which faces the crown portion 23, has formed therein a plurality of notches 28a, b, and c arranged in side-by-side relation. The depth of each notch is less than the thickness of the flange at that location. A plurality of notches are disposed adjacent each exterior side of the helmet in the vicinity of the ears of the wearer. Furthermore, each group of notches is disposed rearwardly from the visor 25. The function of the notches 28a–c will be discussed more fully hereinafter.

The various components comprising the improved attaching assembly are shown more clearly in exploded relation in FIG. 6. A pair of assemblies 20 is normally utilized with a safety helmet 21 when attaching a protective device 22 thereto. The assemblies 20 are of basically the same structure and, as shown, each includes a bracket 30 and an arm or link member 31 pivotally connected thereto. The bracket is preferably of one piece construction and molded of suitable plastic material (e.g., nylon). The bracket includes a base portion 32 which is normally disposed in an upright position, and the interior surface thereof is adapted to supportingly and slidingly engage the adjacent exterior surface of the crown portion 23 of the helmet when the assembly 20 is properly mounted thereon.

Extending laterally in opposite directions from the bottom of the base portion 32 is a pair of first extensions 33,34. A second extension 35 is also provided which is disposed between and offset from extensions 33,34 and depends from the bottom of the base portion 32. When the assembly 20 is mounted on the helmet, the first extensions 33,34 are slidably disposed within a segment of the trough T, and the second extension 35 overlies the top of the trough and slidably engages the exterior side of the flange 24.

Extension 33 is of resilient construction and is the lead extension when the assembly 20 is being mounted on the helmet. That is to say, the distal end 33a of extension 33 initially enters the trough T at the tapered end 24a of the flange 24 and then moves longitudinally of the trough. As the distal end 33a moves longitudinally along the trough, the upper edge 24b of the flange 24 will pass under the upper offset portion 35a of extension 35 while the remainder of the extension will slidably engage the exterior surface of the flange 24. Subsequent to the extension 35 engaging the flange 24 in the manner as described, the extension 34 will be aligned with the trough T and enter same at the tapered end 24a of the flange. The bracket 30 will be manually moved endwise of the trough in the direction indicated by the arrow X in FIG. 4 until the transverse protuberance 33b formed on the distal end 33a of the extension 33 interlocks with a selected one of the notches 28a–c formed in the flange 24. Once the protuberance 33b is in interlocking relation with a selected notch, the bracket 30 is restrained from further endwise movement along trough T. Because of the inherent resilience of extension 33, the protuberance 33b will snap into engagement with the selected notch once it is in alignment therewith. To release the protuberance 33b from the selected notch requires finger pressure being applied in the direction of arrow Y, see FIG. 5, to an exposed button 33c formed on the upper part of distal end 33a and cause the latter to be deflected inwardly towards the exposed surface of the helmet crown portion 23. To permit the necessary deflection required to disengage the protuberance 33b from a notch, it is necessary that the thickness of extension 33 be substantially less than the spacing between the flange 24 and the opposing segment of the exterior surface of the crown portion 23. The extension 33 in a fully deflected state is shown in phantom lines in FIG. 5.

It will be noted in FIG. 5 that flange 24 may be provided with a stop 36 which extends a short distance into the trough T. The stop is disposed adjacent the endmost notch 28c, which is furthest removed from the tapered end 24a of the flange. The number, relative location, and configuration of the notches may vary from that shown without departing from the scope of the invention.

Because of the resiliency of extension 33 and its relative location with respect to extensions 34,35, the flange will be snugly gripped by the bracket 30. In view of this fact, the bracket might be utilized with a flange wherein no notches and stop are provided. In this latter situation, the bracket will be retained in the desired position due to friction alone between the extensions and the flange.

Figure 10:
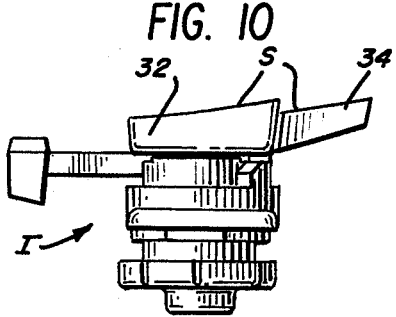
FIG. 10 is a top plan view of the attaching assembly of FIG. 7.

As noted in FIG. 10, the corresponding interior surfaces S of the base portion 32 and extension 34 are shaped so as to conform substantially to the configuration of the surface of the crown portion 23 engaged thereby. Thus, in the illustrated embodiment, there is one bracket which is particularly suited for use on the left side of the helmet and one for use on the right side. The bracket illustrated in FIG. 10 is for the left side of the helmet when the latter is viewed from the visor end.

The thickness of extension 34, as contrasted to that of extension 33, is substantially the same as the spacing between the flange and opposed exterior surface of the crown portion. Thus, the extension 34 prevents the bracket from wobbling once it is disposed within the trough T.

The distal end 35b of extension 35 is curved inwardly a slight amount, see FIGS. 12–14, so as to partially subtend and slidably engage the web 27 when the bracket is mounted on the helmet. Thus, the distal end 35b prevents the bracket 30 moving upwardly relative to the flange 24 and becoming accidentally disengaged therefrom.

Base portion 32, as seen in FIG. 6, is provided with an opening 32a which is adapted to accommodate a portion 37a of the shank 37b of a connecting bolt 37. The end of the opening 32a adjacent the exterior surface of the helmet crown portion 23 is recessed so that the head end of the bolt will not contact the exterior surface of the helmet crown portion 23. The square-shaped, or facetted, portion 37c of the shank 37b is adapted to snugly fit within a similarly shaped opening 31a formed in one end portion 31b of the link member 31, see FIGS. 6 and 16. The threaded end portion 37d of the bolt shank 37b is of sufficient length that it wll protrude a substantial distance beyond the front face of link member 31, as will be described hereinafter. The bolt is preferably formed of a suitable plastic material (e.g., nylon).

Positioned below the opening 32a and protruding outwardly from the front face of the bracket base portion 32 is a ledge 32b having a rounded, or concave, upper surface, the center of curvature of which coincides with the axis of the bolt shank 37b. The ledge upper surface partially encompasses the periphery of a stepped collar 31c protruding rearwardly from the back side of the link member lower end portion 31b, see FIG. 6. The ledge 32b in the illustrated embodiment is made integral with the offset portion 35a of the extension 35, see FIGS. 6 and 12.

Spaced above ledge 32b and disposed to one side of opening 32a and protruding from the front face of the bracket base portion is a lug 32c. The lug is adapted to engage certain portions of the link member in a manner to be hereinafter described so as to confine the pivotal movement of the link member relative to the bracket to within a predetermined sector.

Figure 7:
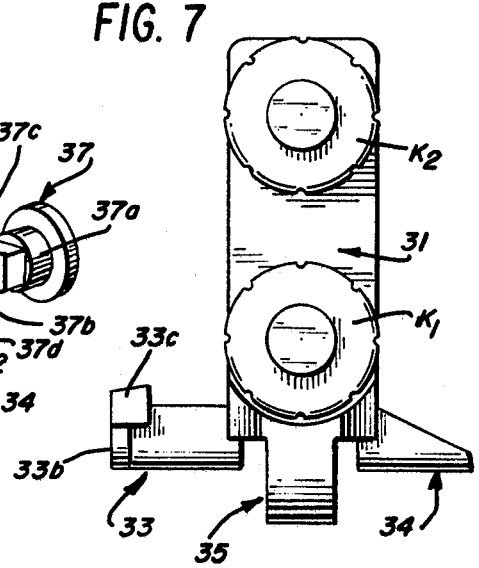
FIG. 7 is an enlarged front elevational view of the attaching assembly of FIG. 1 with a component thereof in a first position of pivotal adjustment.

The link member 31 is of one piece construction, preferably molded from a suitable plastic material (e.g., nylon). As seen in FIG. 18, the stepped collar 31c formed on the back face of link member 31 is provided with a pair of annularly spaced protuberances 31d, 31e. The protuberances are disposed in the circular step formed in the collar and are adapted to engage the lug 32c formed in the front face of the bracket base portion 32. When the link member is in the upright position I, as shown in FIGS. 7, 10, 12, protuberance 31d will engage the upper surface of lug 32c. As seen in FIG. 1, when link member 31 is in position I, the protective device 22 is in an inoperative, or fully raised, position with respect to the safety helmet 21.

Figure 8:
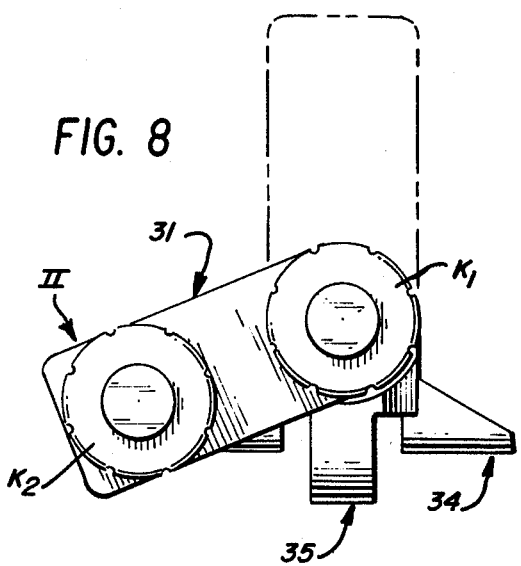
FIG. 8 is similar to FIG. 7 but showing the component in a second position of pivotal adjustment; the said component in the first position of pivotal adjustment being shown in phantom lines.
Figure 9:
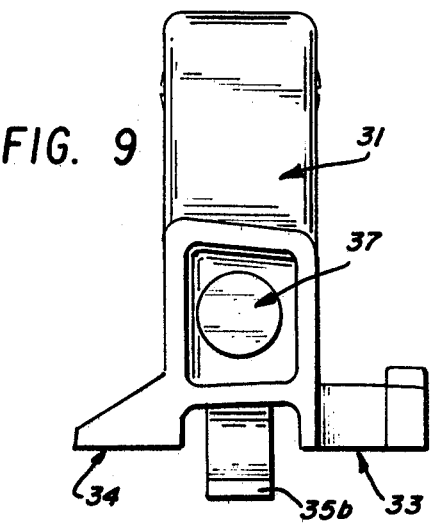
FIG. 9 is an enlarged rear elevational view of the attaching assembly of FIG. 7.
Figure 11:
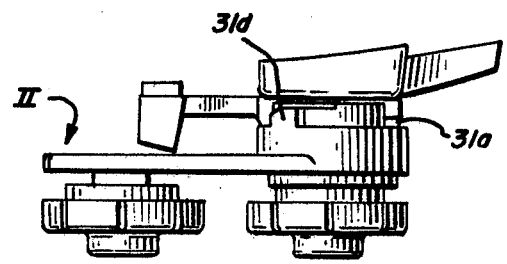
FIG. 11 is a top plan view of the attaching assembly of FIG. 8.

When, however, link member 31 has been pivoted from position I in a counterclockwise direction to the fullest extent so that it assumes position II, see FIGS. 8, 11, 14, protuberance 31e will engage the under surface of lug 32c.

The front face of link member 31, as seen in FIGS. 6, 16, has formed therein an annular recess 31f which is concentrically disposed with respect to opening 31a; the latter being formed in end portion 31b. The opposite end of the link member has protruding outwardly therefrom a threaded stud 31g with a square, or facetted, collar 31h adjacent to and integral with the front face of the link member. The collar shape corresponds to the shape of the opening formed in the side of the protective device (secondary unit) which is being attached to the safety helmet (primary unit), see FIG. 1. The spacing between the opening 31a and the stud 31g formed in the link member may vary from that shown, but should be sufficient so that the protective device will not interfere with the manual adjustment of knob $K_1$, the latter to be hereinafter described.

The resistance to pivotal movement of link member 31 relative to bracket 30 may be varied by the amount of pressure exerted by knob $K_1$ on a pair of washers 38, 40 which encompass the threaded shank portion 37d of bolt 37 and are adapted to fit within the annular recess 31f formed in the front face of link member 31. The knob $K_1$ threadably engages shank portion 37d of bolt 37.

Washer 38 has a ringlike configuration and is formed of a suitable compressible rubberlike material. The back surface 38a of washer 38 frictionally engages the base surface of recess 31f, and the outer surface 38b of the washer engages washer 40. The base surface of recess 31f may be roughened, if desired, to improve the frictional engagement between the washer 38 and the base surface.

Washer 40 is preferably molded from a suitable plastic material (e.g., nylon) and in the illustrated embodiment has a cup-shaped configuration. The base surface 40a of the washer 40 has a suitable opening 40b to accommodate bolt shank portion 37d. An annular side 40c of washer 40 encompasses the periphery of washer 38 and extends into recess 31f. The extent to which the annular side 40c projects from base surface 40a is less than the thickness of washer 38, thus assuring frictional contact between washer 38 and the base surface of recess 31f.

It will be noted in FIGS. 6, 15, that the outer surface of washer 40 is provided with a radially extending rib 40d which is adapted to engage and be disposed in one of the radial grooves 41 formed on the inner surface of knob $K_1$, see FIG. 15a. The opposite, or inner, surface of washer 40 is provided with a projection 40e, see FIG. 15, which is adapted to frictionally engage a surface of washer 38. Thus, when knob $K_1$ has been threaded onto the bolt shank portion 37d so as to produce the desired friction between washers 38, 40 and the base surface of the link member recess 31f, rib 40d will be resiliently held in a groove 41, thereby restraining accidental unthreading or loosening of the knob $K_1$ with respect to shank portion 37d.

While, in the illustrated embodiment, the rib and grooves are radially extending, they are not limited to such a configuration but, instead, the rib may be substituted by a projection having, for example, a semispherical configuration, and the groove, in turn, being replaced by a recess of compatible configuration. Furthermore, the groove or recess may be formed in the outer surface of washer 40, and the rib or projection, in turn, formed on the inner surface of knob $K_1$. In either arrangement, the knob will be releasably locked in a desired threaded position on the shank of bolt 37.

To facilitate positioning of the link member 31 in its upright position I, it will be noted in FIGS. 17, 18, that the surfaces of the bracket and link member, which engage one another, may be provided with complemental embossments 32d and 31i, respectively, which project a short distance from the respective surfaces and are adapted to mate with one another when the link member 31 assumes position I. Each of the embossments may have a circular ring sector configuration, as indicated in the illustrated embodiment. The embossments are particularly useful when the knob $K_1$ is adjusted so that the protective unit can be moved from an inoperative position to an operative position by the wearer of the safety helmet making a sudden nodding motion.

Knob $K_2$ may be similar in configuration to that of knob $K_1$ and may, if desired, be used in combination with washers, not shown, such as washers 38,40. Knob $K_2$ is threaded onto the stud 31g and sandwiches a portion of the protective unit 22 between the link member end portion and the knob $K_2$. Because of the square-shaped, or facetted, configuration of collar 31h, the protective unit 22 will remain in a fixed relative position with respect to the link member. Where, however, it is desired that the protective unit be adjustable relative to the link member, collar 31h may be omitted or it may have a cylindrical shape. In such a situation, the protective unit would be retained in a selected relative position by the friction created by threading the knob $K_2$ tightly on the end of the stud 31g.

In certain instances of attaching the secondary unit to the primary unit, the link member 31 may be eliminated and the secondary unit connected directly to the bracket 30 by the bolt 37. In this type of an arrangement, the bracket base portion 32 might be modified slightly by removing the ledge 32b, so that the outer surface of the base portion and the inner surface of the secondary unit will be in proper face-to-face contact. To maintain the secondary unit in a selected relative position with respect to the bracket base portion, washer 38 will frictionally engage the exterior surface of the secondary unit as the knob $K_1$ is drawn up tight on the shank portion 37d and the washer 40 is pressed against washer 38.

As aforenoted, all of the assembly components, with the exception of washer 38, are preferably molded or formed from a suitable plastic material such as nylon. By reason of this fact, the assembly components are inexpensive, strong, lightweight and not susceptible to malfunctioning due to rusting, corrosion, or the like. Furthermore, the shape, size, and number of the various components of the attaching assembly may vary from that shown and will depend upon the types of primary and secondary units involved. The attaching assembly permits the secondary unit to readily assume a wide range of relative positions with respect to the primary unit. The attaching assembly may also be easily adjusted with respect to or be disassembled from either the primary unit or secondary unit without requiring special tools or an inordinate amount of manual effort.

I claim:

1. An assembly for use in attaching a secondary unit to a primary unit wherein the latter is provided with an exterior wall surface and a flange extending from the wall surface and disposed in spaced, substantially face-to-face relation with the wall surface; said assembly comprising at least one removable bracket having a base portion adapted to slidably engage the wall surface, and releasable means extending from said base portion for disposition between the flange and the wall surface and slidably engaging the flange and retaining the bracket in predetermined positions on the primary unit; and means coacting with the bracket base portion for connecting the secondary unit thereto.

2. The assembly of claim 1 wherein the releasable means extending from the base portion includes at least one first extension extending laterally from the bracket base portion for slidable disposition between the flange and wall surface of the primary unit, and a second extension offset from said first extension for disposition outwardly of the flange and in slidable engagement therewith.

3. The assembly of claim 2 wherein the releasable means includes a pair of first extensions extending laterally in opposite directions from said bracket base portion, and said second extension is disposed intermediate said first extensions.

4. The assembly of claim 3 wherein one of the first extensions is of resilient construction and is adapted to coact with the second extension to resiliently grip the flange between said first and second extensions when said bracket is assembled on the primary unit.

5. The assembly of claim 1 wherein the means for connecting the secondary unit to the bracket base portion includes a manually adjustable first component; a second component mounted on said base portion, said components being in threaded engagement with one another; and washer means disposed intermediate said components and having a surface thereof resiliently contacting a surface of said first component when said components are in predetermined threaded engagement; the contacting surfaces of said washer means and said first component being provided with coacting complemental means for releasably retaining said components in said predetermined threaded engagement.

6. An assembly for use in attaching a secondary unit to a primary unit, said assembly comprising a manually adjustable first component adapted to be disposed adjacent an exterior surface of the secondary unit; a second component adapted to be carried by the primary unit, said components being in threaded engagement with one another and having a segment of the secondary unit adapted to be sandwiched between said first component and a portion of the second component; and washer means disposed intermediate said first component and the portion of the second component, said washer means having a first surface resiliently contacting a surface of said first component, and a second surface adapted to resiliently contact the exterior surface of the secondary unit, when said components are in a predetermined threaded engagement, the contacting surfaces of said washer means and said first component being provided with coacting complemental means releasably retaining the components in said predetermined threaded engagement.

7. The assembly of claim 6 wherein the coacting complemental means provided on the contacting surfaces of said washer means and said first component include a protuberance formed on one of the surfaces and an indentation formed on the other surface, said protuberance being disposed in said indentation when the components are in said predetermined threaded engagement.

8. The assembly of claim 7 wherein the protuberance and indentation extend radially from an axis about which said components are threaded.

9. The assembly of claim 1 wherein the means coacting with the bracket base portion for connecting the secondary unit thereto includes a link member having a first portion pivotally connected to the bracket base portion and a second portion spaced from said first portion and adapted to be connected to the secondary unit; coacting means mounted on said link member and said bracket base portion and limiting relative pivotal movement of said link member within a predetermined sector; and manually adjustable means for varying the amount of surface friction between the bracket base portion and the pivoting link member.

10. The combination of a primary unit having an exterior wall surface provided with a flange extending therefrom and disposed in spaced, substantially face-to-face relation with the exterior wall surface, a secondary unit having a surface thereof outwardly spaced from the exterior surface of the primary unit, and an assembly removably attaching the secondary unit to the primary unit; said assembly comprising a removable bracket slidably mounted on the flange of the primary unit, said bracket including a base portion engaging the exterior wall surface of the primary unit, at least one first extension extending laterally from the base portion and being slidably disposed between the exterior wall surface and the flange of said primary unit, and a second extension offset from said first extension and disposed outwardly from but in slidable contact with the flange, said extensions coacting to resiliently grip the flange therebetween and retain said bracket in a predetermined position with respect to said flange; and adjustable means coacting with said bracket base portion for connecting said secondary unit thereto.

11. The combination of claim 10 wherein the flange of the primary unit is of elongated configuration and the first extension of said bracket is of resilient construction; the surface of said flange adjacent the exterior wall surface and an adjacent surface of the first extension being provided with complemental locking means coacting with one another when said bracket assumes said predetermined position with respect to said flange.

12. The combination of claim 11 wherein the complemental locking means includes a plurality of longitudinally spaced notches formed in said flange surface and the adjacent surface of said first extension being provided with a protuberance resiliently accommodated in a selected notch when said bracket is disposed in a predetermined position relative to said flange.

13. The combination of claim 11 wherein the primary unit is a helmet having a substantially rigid gutterlike rim partially encompassing the lower edge thereof, said rim having a gap formed therein and the secondary unit is a protective device adapted to be adjusted relative to the helmet between operative and inoperative positions with respect to the head of the wearer of the helmet.

14. The combination of claim 13 wherein the bracket is mounted on and removed from the helmet rim upon moving said bracket through the gap formed therein.

15. The combination of claim 14 wherein the assembly includes a pair of brackets slidably disposed in predetermined spaced locations on said helmet rim; each bracket and the helmet rim at each location being provided with complemental locking means for releasably retaining the bracket at said location.

16. The combination of claim 15 wherein the helmet is of molded one piece substantially rigid construction, and the complemental locking means at each predetermined location on said rim comprises at least one notch formed in the surface thereof; the depth of said notch being less than the thickness of said rim at said location.

17. The combination of claim 14 wherein said helmet is provided with a visor located at the gap formed in said rim.

18. The combination of claim 13 wherein the adjustable means coacting with the bracket base portion for connecting the protective device thereto includes an elongated link member having one end thereof pivotally connected to the base portion and the opposite end thereof connected to the protective device; a manually adjustable first component; a second component mounted on said bracket base portion and being in threaded engagement with said first component, said link member one end being disposed intermediate said first component and a portion of said second component; and washer means disposed intermediate said first component and said link member one end, said washer means having a first surface resiliently contacting a surface of said first component, and a second surface resiliently contacting said link member one end, when said first and second components are in a predetermined threaded engagement.

19. The combination of claim 18 wherein the contacting surfaces of said washer means and said first component are provided with coacting complemental means releasably retaining the components in said predetermined threaded engagement.

20. The combination of claim 19 wherein the link member one end and the bracket base portion are in surface-to-surface contact with one another, said contacting surfaces being provided with complemental means coacting with one another to releasably retain said link member in a predetermined position of pivotal adjustment with respect to said bracket base portion.

* * * * *